United States Patent [19]

Schaffer et al.

[11] Patent Number: 4,729,382
[45] Date of Patent: Mar. 8, 1988

[54] METHOD AND APPARATUS FOR AUTOMATICALLY DETERMINING PULSE RATE AND DIASTOLIC AND SYSTOLIC BLOOD PRESSURE

[76] Inventors: John D. Schaffer, 5601 Pinellas Dr., Knoxville, Tenn. 37919; George L. McDade, Rte. 17, Fox Park Rd., Knoxville, Tenn. 37921

[21] Appl. No.: 902,705

[22] Filed: Sep. 2, 1986

[51] Int. Cl.$^4$ .............................................. A61B 5/02
[52] U.S. Cl. .................... 128/679; 128/681; 128/682; 128/687
[58] Field of Search ............. 128/672, 677, 678–686, 128/687, 689

[56] References Cited

U.S. PATENT DOCUMENTS

| | | | |
|---|---|---|---|
| 2,297,905 | 10/1942 | Luisada | 128/681 X |
| 2,989,051 | 6/1961 | Zuidema et al. | 128/681 X |
| 3,104,661 | 9/1963 | Halpern | 128/679 X |
| 3,157,177 | 11/1964 | Smith | 128/679 |
| 3,348,534 | 10/1967 | Mark et al. | 128/679 |
| 3,581,734 | 6/1971 | Croslin et al. | 128/679 |
| 3,905,354 | 9/1975 | Lichowsky | 128/681 |
| 3,920,004 | 11/1975 | Nakayama | 128/680 |
| 3,978,848 | 9/1976 | Yen et al. | 128/681 |
| 4,009,709 | 3/1977 | Link et al. | 128/683 X |
| 4,290,434 | 9/1981 | Jewett | 128/680 |
| 4,313,445 | 2/1982 | Georgi | 128/680 |
| 4,349,034 | 9/1982 | Ramsey, III | 128/681 |
| 4,360,029 | 11/1982 | Ramsey, III | 128/681 |
| 4,417,586 | 11/1983 | Jewett | 128/680 |
| 4,479,494 | 10/1984 | McEwen | 128/682 X |
| 4,566,463 | 1/1986 | Taniguchi et al. | 128/687 X |

Primary Examiner—Edward M. Coven
Assistant Examiner—Angela D. Sykes
Attorney, Agent, or Firm—Ronald L. Lyons

[57] ABSTRACT

An apparatus and method is disclosed for automatically determining the pulse rate and systolic and diastolic blood pressure. The apparatus comprises a device for detecting arterial pulsations in a subject's body. The improvement comprising a sensor in a pressurized bladder and responsive to arterially induced pressure pulsations. The sensor comprises a pressure transducer chamber and a pressure transducer. The pressure transducer chamber contains a pressure equalization passageway communicating with the interior of the bladder and the interior of the pressure transducer chamber. The pressure equalization passageway equalizes the pressure between the bladder and the chamber to prevent the pressure in the bladder from impending upon the pressure transducer. A method is disclosed for automatically determining pulse rate and systolic and diastolic blood pressure. Pulsation generated and pressure generated signals and time durations are stored and then used to calculate the subjects pulse rate, systolic blood pressure and diastolic blood pressure.

23 Claims, 8 Drawing Figures

METHOD AND APPARATUS FOR AUTOMATICALLY DETERMINING PULSE RATE AND DIASTOLIC AND SYSTOLIC BLOOD PRESSURE

BACKGROUND OF THE INVENTION

1. Field of the Invention

This invention relates to an automatic apparatus and method for detecting arterially-induced pulsations and automatically determining the pulse rate, and systolic and diastolic blood pressure.

2. Description of the Prior Art

It is known in the prior art that arterially-induced pressure pulsations may be detected by means of an electrostatic microphone responding to the pressure pulsations in a compressing fluid as disclosed in Bouche U.S. Pat. No. 2,851,030. Further, the use of microphones and electrostatic pressure conversion elements are disclosed in Luisada U.S. Pat. No. 2,297,905 and Speaker, et al U.S. Pat. No. 2,452,799. Further, Zuidena U.S. Pat. No. 2,989,051 uses pulsation pressure information along with cuff pressure information to derive blood pressure reading. Utilizing this same approach in most recent art is shown in the following references: German Pat. No. 3,008,601; Nakayama U.S. Pat. No. 3,920,004; Link et al U.S. Pat. No. 4,009,709; Link et al U.S. Pat. No. 4,074,711; Wohltjen et al U.S. Pat. No. 4,078,551; Gangirard et al U.S. Pat. No. 4,177,801; Danna et al U.S. Pat. No. 4,261,368; Jewett U.S. Pat. No. 4,290,434; Ramsey III U.S. Pat. No. 4,349,034; Ramsey III U.S. Pat. No. 4,360,029; Jewett U.S. Pat. No. 4,417,586; Nunn et al U.S. Pat. No. 4,427,013.

The need to measure both the systolic and diastolic blood pressure and the pulse rate utilizing an automatic procedure was required.

A unique method for not only determining the pulse rate but determining the systolic and diastolic blood pressure was discovered.

It was further discovered that upon inflating the bladders in the instant invention that the pressure within the bladder would impend upon the pressure transducer. More specifically, the pressure inside the bladder impends upon a diaphragm located in the pressure transducer, preventing the diaphragm from responding to arterially-induced pressure pulsations in the bladder. The inflation pressure which is much greater than the arterially-induced pressure pulsations in the bladder, interferes or prevents the diaphragm from reacting or flexing in response to these arterially-induced pulsations. It was discovered that a pressure equalization passageway was necessary in order to equalize the pressure between the interior of the bladder and the interior of the pressure transducer chamber. This passageway allows equalization of pressure on both sides of the pressure transducer diaphragm. The size of the passageway is critical since it must be of a sufficient size to allow pressure equalization between the inflation pressure in the bladder and the interior of the pressure transducer chamber and not interfere with the pressure transducer diaphragm reacting to or sensing the arterially-induced pulsations generated in the bladder. Further, it was discovered that pressure transducers have different sensitivities to arterially-induced pulsation amplitudes. Consequently a device was discovered for use in conjunction with the instant sensor for decreasing the amplitude of the arterially-induced pulsation amplitudes such that pressure transducers of varying sensitivity may be used.

The prior art disclosed many methods for determining blood pressure and pulse rate, three of the most pertinent prior art references are the following: Croslin U.S. Pat. No. 4,271,844; Croslin U.S. Pat. No. 4,326,537 and Croslin U.S. Pat. No. 4,407,297. These are all related companion patents.

In the above mentioned patents, each is comparing the detective sequence of the relative amplitudes of a predetermined number of blood pressure pulses with a plurality of known valid sequences to determine if the detected sequences are valid. In the instant invention, the above known valid sequences, is not a fixed number derived from data. Further, in the above patents, if the detected sequence is determined to be valid, then the systolic pressure is determined to be the registered occluding pressure at the onset of a predetermined blood pressure pulse. This determination of the occluding pressure in the instant invention is determined at a different point of reference. Further, as set forth in these references, in determining the diastolic pressure, to be the registered occluding pressure at the onset of a preselected pulse, in a predetermined number of last pulses when the representative value is less than the threshold value, this does not disclose the instant method. Further, and most imporantly, these patents are concerned with the detection of the Korotkoff sound whereas the instant invention is concerned with detecting arterially-induced pressure pulsations as distinguished from audio sound detection. Further, in the above patents, these methods are registering the value of a sample which is generated at the start of a blood pressure pulse and maintained for the duration of at least several, but not all, of the succeeding blood pressure pulses. In the instant invention, all the arterially-induced pulsations and pressures are stored and used to compute blood pressure values and pulse rate after the cycle has been completed. In the above patents, these methods are merely taking a window from the data and using the figures from this window to determine blood pressure. The methods disclosed in the above patents are discarding all the other readings outside this window area. Further, these patents are deriving the "height" of a blood pressure pulse by substracting the respective value registered in their step (c) from the larger sample value of the respective blood pressure pulse and maintaining such height for the duration of at least several, if not all, of succeeding blood pressure pulses and then taking slight variations on that one sensor signal. In the instant method, there are separate sensors used in determining the occluding and diastolic pressure and the systolic pressure.

As to U.S. Pat. No. 3,978,848 which discloses a blood pressure and rate monitor wherein the inflatable cuff contains a pressure responsive transducer that performs two functions. The first function is providing a first signal corresponding to the gauge pressure in the cuff and the second function provides a second signal corresponding to variation in the cuff pressure produced by expansion and contraction of the occluding artery due to the pumping action of the heart.

U.S. Pat. No. 3,905,354 claims a method of automatically measuring the patient's systolic and diastolic blood pressure by several steps including generating quantized pressure signals in response to pressure pulses to provide individually defined pressure signals of a uniform amplitude.

In both U.S. Pat. No. 3,978,848 and U.S. Pat. No. 3,905,354 neither disclose apparatuses or methods for aleviating the problem of the bladder inflation pressure impending upon the pressure transducer thereby preventing the pressure transducer from detecting arterially-induced pulsations and generating electrical signals having amplitudes corresponding to the pulsations. Further, the above prior art discloses no apparatus or method for adjusting the sensitivity of pressure transducers to the amplitudes of these pulsations. Further, the above prior art does not disclose or suggest the instant method.

SUMMARY OF THE INVENTION

It is a primary object of the present invention to provide an automatic apparatus and method for determining, pulse rate and systolic and diastolic blood pressure. The apparatus, the sensors of which, are not prevented from sensing arterially-induced pressure pulsations by bladder inflatable pressure. A further object of the invention is to provide a method for utilizing the entire arterially-induced pulsations history and pressure history within the bladder received from sensors within an apparatus to determine pulse rate and systolic and diastolic blood pressure.

The principal upon which the present device is based is first explained. The device is an automatic device for measuring pulse rate and the systolic and diastolic blood pressures of a human subject. The human subject preferably places his left arm into a rigid cylindrical shell preferably containing two inflatable bladders. The first and second bladders being positioned such that the second bladder when inflated occludes the blood flow to the first bladder. Consequently, the second bladder is located closest to the elbow of the subject and the first bladder is located closest to the hand of a subject, when the subject's forearm is placed into a rigid cylindrical shell containing the two bladders. The subject presses a start button on the apparatus which energizes a microcomputer. The computer energizes a pressure pump which pumps fluid into a fluid volume chamber. The fluid is preferably air. The fluid volume chamber allows fluid to escape through two orifices which are connected separately via fluid tubes or air tubes to each of the two inflatable bladders. As the fluid chamber fills with fluid both the first and second bladders simultaneously fill with fluid or air. The second bladder refered to as the occluding bladder or diastolic bladder additionally is connected via a fluid or air tube to a gauge pressure transducer which is connected to the microcomputer. Both the first and second bladder continue to be inflated by fluid from the fluid volume chamber to a pressure at which the second bladder occludes blood flow. During the inflation step, at a predetermined pressure, the microcomputer begins to process electrical signals generated by the sensors in both bladders. The occluding of blood flow by the second bladder results in the sensor in the first bladder sensing no arterially-induced pressure pulsation amplitudes. At this point, the microcomputer de-energizes the pressure pump and inflation ceases. Then the microcomputer energizes a solenoid valve connected to the fluid volume chamber. This solenoid valve opens and air or fluid is released, at a predetermined rate, from the fluid volume chamber through a deflation control orifice. As this fluid is released from the fluid volume chamber deflation begins in the first and second bladders at the same predetermined rate. During both the inflation and deflation step the microcomputer receives and stores electrical signals from the sensors in both bladders. The electrical signals from the sensors have amplitudes corresponding to the pulsation in the bladders. The gauge pressure transducer, located in fluid communication with the second bladder generates electrical signals corresponding to the pressure in the second bladder and sends these electrical signals to the microcomputer. Further, the time duration between each pulsation amplitude is received and stored by the microcomputer. These electrical signals and time durations are processed by the microcomputer after the deflation step has been completed. At a predetermined pressure the deflation step is terminated. At the end of the deflation step, the microcomputer activates two solenoid valves. One of these valves is located in the fluid or air line or tube between the fluid volume chamber and the first bladder. The other solenoid valve is located in the fluid or air line or tube between the fluid volume chamber and the second bladder. These valves are opened to allow fluid in the system in both bladders to escape. At this point the subject may remove the forearm from the rigid cylindrical shell since the bladders have now been completely deflated. After completion of the above procedures, the microcomputer processes all the stored signals and time durations and then calculates the subject's pulse rate, systolic blood pressure and diastolic blood pressure. The processing and calculating involves the steps of first determining the systolic pressure of the subject by determining inflation pressure in the second bladder when the first pulsation is detected in the first bladder after deflation begins. This pressure is the systolic pressure. Secondly, the amplitudes of all the pulsations detected in the second bladder during the deflation step are examined. This process includes first determining an increase in these amplitudes and then a decrease in these amplitudes and then a constant series of amplitudes. The diastolic pressure of the subject is determined by determining the inflation pressure in the second bladder when the first pulsation at the beginning of the series of constant amplitudes is detected in the second bladder. This is the diastolic pressure of the subject. Then the time duration between all of the pulsations during the deflation step is examined and processed to determined the subject's pulse rate. More preferably, the time duration between the maximum amplitudes of the last eight arterially-induced pressure pulsations in the second bladder before the conclusion of the deflation step are measured and this is used to determine the average time duration between pulsations. The average time duration is divided into 60 to calculate the number of pulses per minute, i.e., pulse rate. The above described microcomputer controlled arterially-induced pulsation and pressure monitor, utilizes software control to perform the above method.

The foregoing and other objects, the features and the advantages of the present invention will be pointed out in, or apparent from, the following description of the preferred embodiments considered together with the accompanying drawings.

DESCRIPTION OF THE PREFERRED EMBODIMENT

A preferred embodiment of the present invention will now be described with reference to the Drawings.

Figure 1:
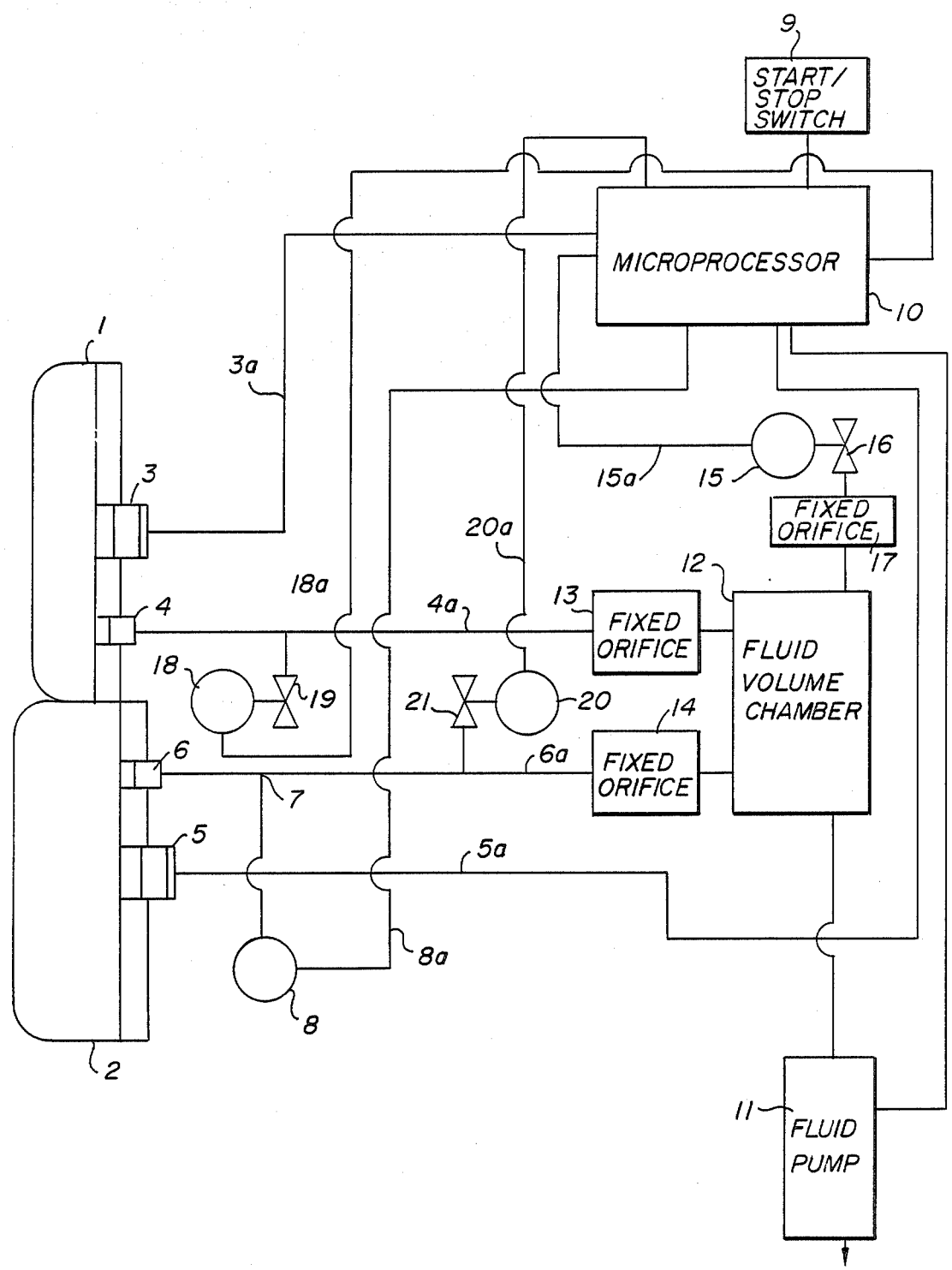
FIG. 1 is a block diagram of a preferred embodiment of the automatic pulse rate, and systolic and diastolic blood pressure measuring apparatus of the instant invention.
Figure 2:
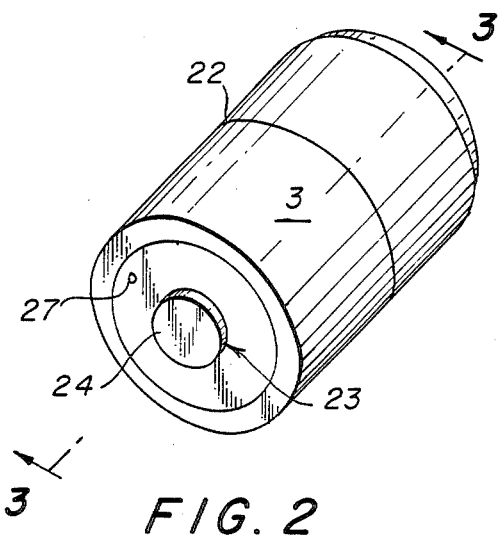
FIG. 2 is greatly enlarged perspective view of a sensor comprising a pressure transducer chamber and a pressure transducer.
Figure 3:
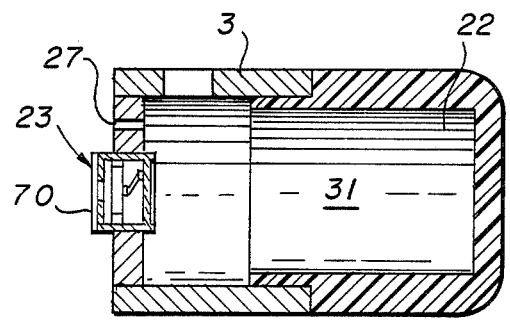
FIG. 3 is a cross-sectional schematic representation of the structure of FIG. 2.
Figure 3A:
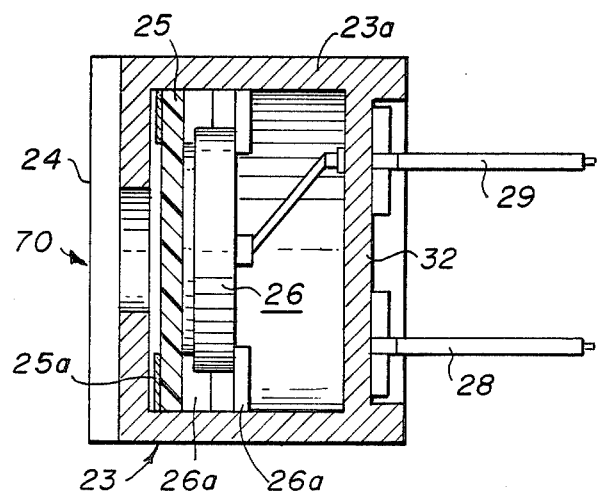
FIG. 3a is a cross-sectional greatly enlarged schematic representation of a portion of FIG. 3 comprising a pressure transducer.
Figure 5:
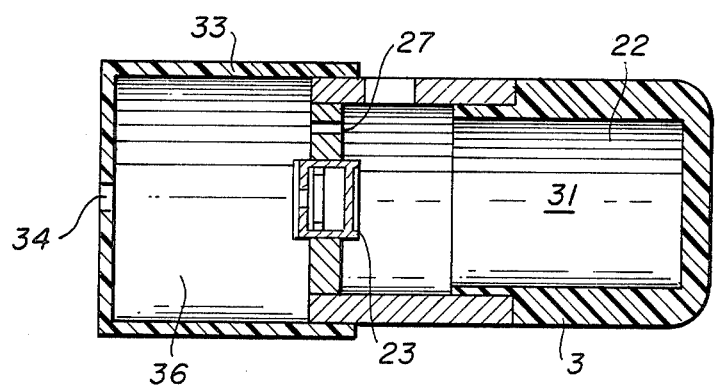
FIG. 5 is a cross-sectional schematic representation of the structure of FIG. 4.
Figure 6:
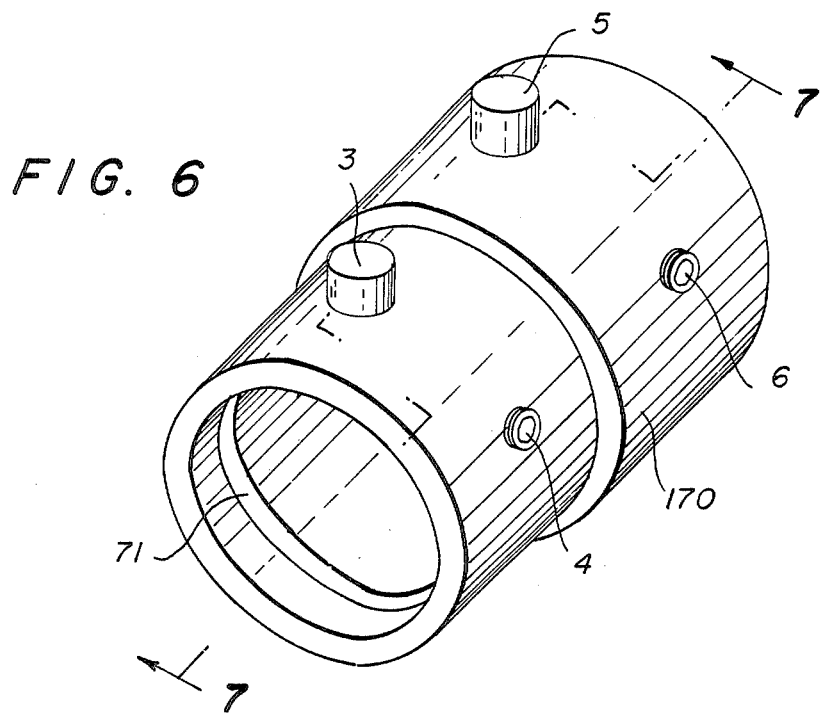
FIG. 6 is an elevated schematic representation of an outer rigid cylindrical shell for encircling a portion of the subject's body containing first and second inflatable bladders, tubular member by which the bladders are inflated and a sensor in each bladder.
Figure 7:
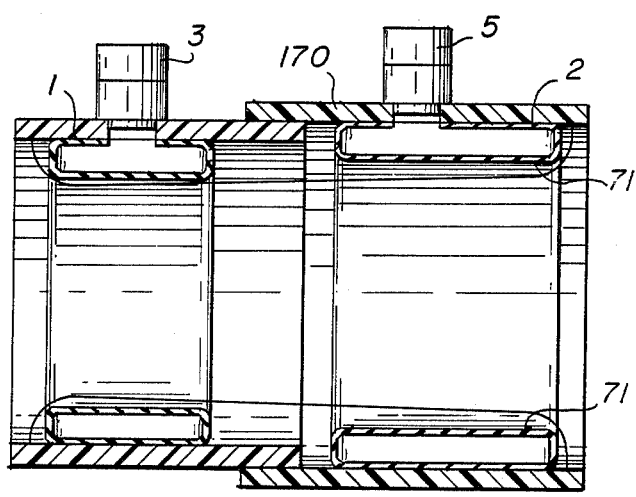
FIG. 7 is a cross-sectional schematic representation of the structure of FIG. 6.

FIG. 1 is a block diagram illustrating the construction of a preferred embodiment of the present invention. FIG. 1, illustrates first bladder 1 located inside cylindrical shell 170 as illustrated in FIGS. 6 and 7 and first bladder 1 as illustrated in FIG. 7 encircles and is secured to the inside circumference of a portion of rigid cylindrical shell 170 as illustrated in FIG. 7. First bladder 1 is sealed to an inside wall inside the rigid outer wall of said cylindrical shell 170. When first bladder 1 is filled with a fluid, it imparts external pressure to a portion of a subject's body such as the lower arm, e.g. the forearm. First bladder 1 contains first sensor 3 which is in fluid communication with the interior of first bladder 1 and which comprises a pressure transducer chamber 22 as illustrated in FIG. 3 and a pressure transducer 23 as illustrated in FIGS. 3 and 3a. First bladder 1 additionally contains fluid passageway 4 which is connected to tubular member 4a which is in fluid communication with fluid volume chamber 12 via orifice 13. First bladder 1 is often referred to as the systolic bladder in that the arterially-induced pressure pulsations generated in bladder 1 and detected by pressure transducer 3 are processed to calculate the systolic pressure. Second bladder is 2 located in relationship to first bladder 1 such that second bladder 2 is the blood occluding bladder. Second bladder 2 when positioned on a portion of the subject's body, such as the forearm, is located nearer to the subject's elbow as compared to first bladder 1 which is located nearer to the subject's hand in relationship to second bladder 2. Second bladder 2 contains second sensor 5 which is in fluid communication with the interior of second bladder 2 and which comprises second pressure transducer chamber 22 as illustrated in FIG. 3 and second pressure transducer 23 as illustrated in FIGS. 3 and 3a. Second bladder 2 further contains fluid passageway 6 which is in communication with the interior of second bladder 2 and connected to tubular member 6a which is in fluid communication with fluid volume chamber 12 via orifice 14. Second bladder 2 additionally is in fluid communications with gauge pressure transducer 8 via fluid or air line or tube at connector 7. Gauge pressure transducer 8 detects the inflation pressure contained in second bladder 2 and generates and transmits an electrical signal corresponding to this pressure to microcomputer 10 via line 8a. The subject to be tested places the arm, preferably the forearm, into a rigid cylindrical shell 170 from second bladder 2 end of the shell as illustrated in FIG. 6. Shell 170 contains a cuff not shown in FIG. 6 but said cuff comprises first bladder 1 and second bladder 2. The cuff is preferably a non-restrictive covering for first bladder 1 and second bladder 2. Referring now to FIG. 1 there is shown, in flow chart form, a preferred method of practicing the principles of the present invention. Start/Stop switch 9 when in the start position activates microcomputer 10 which in turn activates fluid pump 11. Fluid pump 11 pressurizes fluid volume chamber 12. As fluid volume chamber 12 fills with fluid, this fluid passes through fixed orifice 13 and tubular member 4a through fluid passageway 4 and into first bladder 1 thereby inflating first bladder 1. Simultaneously with the inflation of first bladder 1, the fluid from fluid volume chamber 12 passes through fixed orifice 14 and tubular member 6a through fluid passageway 6 and into second bladder 2 thereby inflating second bladder 2. As first bladder 1 and second bladder 2 inflate the pressure in second bladder 2 is detected by gauge pressure transducer 8 which generates electrical signals corresponding to this pressure. These electrical signals are communicated to microcomputer 10 via line 8a. The software control of microcomputer 10 determines the occluding pressure and the pressure at which inflation ceases. Microprocessor 10 monitors the arterially-induced pressure pulsation amplitudes generated in second cuff 2 and detected by second sensor 5 via line 5a. During the inflation step to determine the occluding pressure of the subject microcomputer 10 examines amplitudes of all pulsation detected in the second bladder during the inflation step and first determines an increase in amplitude of these arterially-induced pressure pulsations in second bladder 2 and then determines a decrease in these amplitudes, and then determining the occluding pressure of the subject by determining the inflation pressure in the second bladder when these amplitudes drop below a predetermined level and pulsations cease in the first bladder. This predetermined level is one-half of the maximum amplitude of the arterially-induced pressure pulsations during inflation. This is the occluding pressure. This occluding pressure is the pressure at which the microprocessor 10 de-energizes fluid pump 11. At this point, inflation in both first bladder 1 and second bladder 2 ceases. After inflation ceases, the software in microprocessor 10 activates solenoid 15 via line 15a which opens valve 16 resulting in fluid escaping at a predetermined rate from fluid volume chamber 12 through fixed orifice 17. This begins the deflation of both first bladder 1 and second bladder 2 at a predetermined rate through both fluid passageway 4 and fluid passageway 6. During the deflation step microcomputer 10 continually monitors arterially-induced pressure pulsations in both first bladder 1 and second bladder 2. Further, microprocessor 10 continually monitors the pressure within second bladder 2. It was discovered that when either first bladder 1 or second bladder 2 contains at least 50 mm Hg pressure this pressure interferes with the detection of arterially-induced pressure pulsations by the pressure transducers 23 as illustrated in FIGS. 3 and 3a, located in first bladder 1 and first bladder 2. These pressure transducers are prevented from properly operating, i.e., detecting arterially-induced pressure pulsations by the pressure in the bladders. The inflation pressures within the bladders were pressing against the pressure sensing side of the pressure transducers. These pressure transducers as illustrated in FIGS. 3 and 3a comprise a flexible diaphragm 25 and a stationary plate 26 both illustrated in FIG. 3a. The flexible diaphragm 25 flexes or moves in response to the arterially-induced pressure pulsations generated in the bladder. This flexing or movement by diaphragm 25 in relationship to fixed plate 26 in pressure transducer 23 produces electrical signals having amplitudes corresponding to the amplitudes of the arterially-induced pressure pulsations generated in the bladders. In order to aleviate this problem, it was discovered that pressure equalization passageway 27 as illustrated in FIGS. 2, 3 and 5, was necessary to equalize the pressure between the pressure in the bladders and the internal area 31 of pressure transducer chamber 22 as illustrated in FIGS. 3 and 5. When the pressure in the bladder is equalized with the pressure in the pressure transducer chambers utilizing a pressure equalization passageway of a critical size, the force applied by the inflation pressure within the bladder upon flexible diaphragm 25 in pressure transducer 23 as illustrated in FIG. 3a is eliminated. Pressure transducer diaphragm 25 is free to flex or move in response to each arterially-induced pressure pulsation. As pressure from the bladder passes through pressure equalization passageway 27 and into internal area 31 of chamber 22, this pressure then passes through passageway 27a into the interior of pressure transducer 23. The size or location of passageway 27a is not critical except passageway 27a must be of a size and location that the pressure will remain essentially the same between the interior of pressure transducer 23 and internal area 31 of chamber 22.

During both the inflation step and the deflation step, microcomputer 10 monitors continuously the electrical signals and time durations from the sensors and the gauge pressure transducer. Microcomputer 10 stores these signals and time durations received from first sensor 3, second sensor 5 and gauge pressure transducer 8. During the deflating step gauge pressure transducer 8 continually detects the pressure in second bladder 2 converting these pressure detections into electrical signals. These signals are relayed to microcomputer 10. When a certain pressure, during the deflation step is reached, microprocessor 10 activates both solenoid 18 which opens valve 19 and solenoid 20 which opens valve 21 via lines 18a and 20a respectively, resulting in a rapid decrease in pressure in both first bladder 1 and second bladder 2 and fluid volume chamber 12. The system returns to ambient pressure. When first bladder 1 and second bladder 2 are deflated the subject may remove the forearm from the device. After the release of pressure, microprocessor 10 processes the stored signals and time durations calculating the subject's pulse rate, systolic blood pressure and diastolic blood pressure by first determining the systolic pressure of the subject by determining inflation pressure in said second bladder when the first arterially-induced pressure pulsation is detected in first bladder 1 after the deflation has begun in both bladders. This is the systolic pressure. Secondly microprocessor 10 examines amplitudes of all pulsations detected in the second bladder 2 during the deflation step by first determining an increase in these amplitudes and then determining a decrease in these amplitudes and then observing constant amplitudes and then determining diastolic pressure of the subject by determining the inflation pressure in the second bladder when the first pulsation at the beginning of the constant amplitude series is detected in second bladder 2. This is the diastolic pressure. Microprocessor 10 then examines the time duration all the pulsations during the deflation step and then calculates the pulse rate of the subject.

Refering next to FIG. 2, a sensor is illustrated as sensor 3. Sensor 3 as illustrated in FIG. 2 is identical to sensor 5 as illustrated in FIG. 1. Sensor 3 as illustrated in FIG. 2 comprises transducer 23 and transducer cover 24 located across and over the arterially-induced pressure pulsation sensing end of pressure transducer 23. Pressure transducer 23 is shown projecting through the end of sensor 22 as illustrated in FIG. 2. Pressure equalization passageway 27 is shown passing through the end of sensor 3 as illustrated in FIG. 2.

Refering next to FIG. 3, sensor 3 is in fluid communication with first bladder 1. This is illustrative of sensor 5 as illustrated in FIG. 1 which is in communication with second bladder 2. As illustrated in FIG. 3 first pressure transducer 23 having an arterially pulsing sensing end 70 in fluid communication with the interior of first bladder 1 to detect arterially-induced pressure pulsations in first bladder 1 and to generate first electrical signals having amplitudes corresponding to first bladder 1 pulsations. Pressure transducer 23 has a non-sensing end 32 in communication with the interior 31 of first chamber 22 as illustrated in FIG. 3. It should be understood that sensor 5 as illustrated in FIG. 1 and second pressure transducer located in sensor 5 and in fluid communication with the interior of second bladder 2 operate in the same manner and function the same as sensor 3 and pressure transducer 23 illustrated in FIG. 3. First pressure equalization passageway 27 passing through the end or wall of sensor 3 is in fluid communication with the interior of first bladder 1 and first pressure transducer chamber 22 and interior 31 of first chamber 22. First chamber 22 is in fluid communication with the interior of pressure transducer 23 via passageway 27a as illustrated in FIG. 3a. Pressure equalization passage 27 as illustrated in FIGS. 2 and 3 is of the same size and functions the same as second pressure equalization passageway passing through the end of sensor 5 and in communication with the interior of second bladder 2 and interior 31 of pressure transducer chamber 22 located in sensor 5. First pressure equalization passageway 27 as illustrated in FIG. 3 is of a sufficient size to allow equalization of pressure between said first cuff 1 and first interior 31 of pressure transducer chamber 22 sufficiently to substantially reduce inflation pressure in first cuff 1 from impending upon first pressure transducer 23 without interfering with detection of the arterially-induced pressure pulsations by said first pressure transducer 23 thereby eliminating any interference of inflation pressure with the detection of arterially-induced pressure pulsations in first bladder 1. As mentioned, second sensor 5 as illustrated in FIG. 1, is in fluid communication with second bladder 2 and is responsive to arterially-induced pressure pulsations in second bladder 2 and generates a second electrical signal having an amplitude corresponding to arterially-induced pressure pulsations generated in second bladder 2. Second sensor 5 comprises a second pressure transducer as illustrated in FIG. 3 as pressure transducer 23 having an arterially-induced pressure pulsation sensing end 70 in communication with the interior of second bladder 2 to detect arterially-induced pressure pulsations in second bladder 2 and generate second electrical signals having amplitudes corresponding to bladder 2 arterially-induced pressure pulsations. Pressure transducer 23 located in second sensor 5 has a non-sensing end 32, as illustrated in FIGS. 3 and 3a in communication with interior 31 of second transducer chamber 22 as illustrated in FIG. 3. As mentioned, passageway 27a passing through end 32 as illustrated in FIG. 3a is of a sufficient size and location to equalize pressure between interior 31 of chamber 22 and the interior of pressure transducer 23. Second pressure equalization passageway 27 as illustrated as passing through the end or wall of second chamber 22 is in fluid communication with the interior of second bladder 2 and interior 31 of second pressure transducer chamber 22 as illustrated in FIG. 3. Second pressure equalization passageway 27 is of a sufficient size to allow equalization of pressure between second bladder 2 and interior 31 of second chamber 32 as illustrated in FIG. 3 sufficiently to substantially reduce inflation pressure from impending upon second pressure transducer 23 without interfering with detection of the arterially-induced pressure pulsations by second pressure transducer 23 thereby eliminating any interference of inflation pressure with the detection by second pressure transducer 23 of arterially-induced pressure pulsations in second bladder 2.

Now referring to FIG. 3a, wire 28 is attached to fixed plate 26 in pressure transducer 23. Wire 29 is attached to a conductive material comprising pressure transducer 23 which is attached to flexible conductive diaphragm 25. Wires 28 and 29 are connected electrically to microcomputer 10 as illustrated in FIG. 1 as 5a and 3a.

Figure 4:
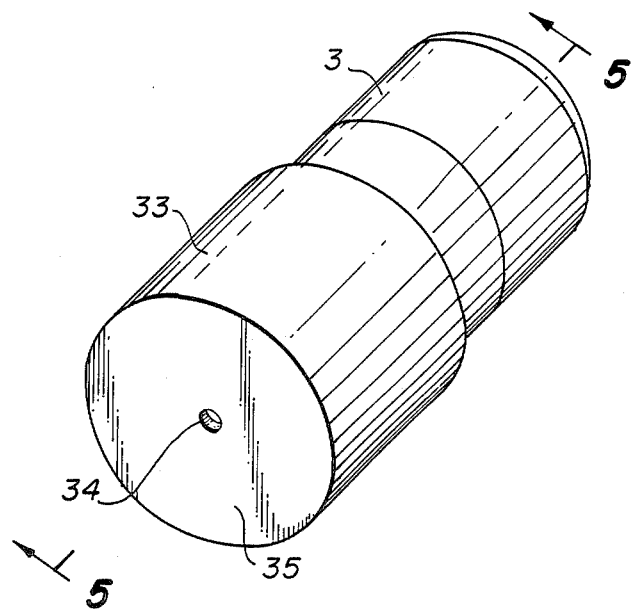
FIG. 4 is a schematic representation similar to FIG. 3 additionally illustrating an attenuator in slideable contact with a sensor.

As to FIG. 4, this is a modification of the sensor device 3 using attenuator 33. Both sensor 3 and sensor 5 may be used with attenuator 33. Attenuator 33 is slipped over the end of sensor 3 as illustrated in FIG. 4. Attenuator 33 contains attenuator passageway 34. It has been found that some pressure transducers are more sensitive to arterially-induced pressure pulsations than others. It may be necessary to adjust the sensitivity of each of the pressure transducers due to the large variation in the amplitudes of the arterially-induced pressure pulsations between subjects. This adjustment may be made by using attenuator 33 as illustrated in FIG. 4. The arterially-induced pressure pulsations can be attenuated before these pulsations reach the pressure transducer by placing attenuator 33 with the attenuator passageway 34 in fluid communication with the inside of the bladder and the pressure transducer. As mentioned, it was found that some pressure transducers are more sensitive than others and the arterially-induced pressure pulsations would "overdrive" some of these pressure transducers. This problem was eliminated using the attenuator.

Now referring to FIG. 3a, pressure transducer 23 is positioned in sensor 3 as illustrated in FIG. 3. Pressure transducer 23 comprises outer electrically conductive shell 23a which contains an opening at end 70 for receiving arterially-induced pressure pulsations generated in the bladders. Inside pressure transducer 23, as illustrated in FIG. 3a, is pressure transducer diaphragm 25 which is as flexible, electrically conductive diaphragm. Diaphragm 25 flexes or moves in response to arterially-induced pressure pulsations generated in bladders 1 and 2 as illustrated in FIG. 1. Diaphragm 25 is in electrical communication with the outer electrical conductive shell of pressure transducer 23 and held in place within pressure transducer 23 by electrical seal 25a. Pressure transducer 23 further contains fixed plate 26. Fixed plate 26 is an electrically conductive plate which is not in electrical communication with said pressure transducer 23. Fixed plate 26 is in electrical communication with said microcomputer 10 via line 28 as illustrated in FIG. 3a. Fixed plate 26 is stationary and does not flex or move in response to arterially-induced pressure pulsations generated in the bladders. Fixed plate 26 is held in place inside pressure transducer 23 by electrical insulators 26a which electrically insulate fixed plate 26 from pressure transducer 23. As pressure from the bladder passes through pressure equalization passageway 27 and into internal area 31 of chamber 22, this pressure must reach the interior of pressure transducer 23. This may be accomplished in a number of ways. The size or location of a passageway between the interior of pressure transducer 23 and interior 31 of chamber 22 is not critical except that the pressure inside pressure transducer 23 should be essentially the same pressure as in internal area 31 of chamber 22. This is illustrated as passageway 27a in FIG. 3a.

The outer shell of pressure transducer 23 is in electrical communication with microcomputer 10 via wire 29. Pressure transducer 23 contains an arterially-induced pressure pulsation sensing end 70 and a non-sensing end 32.

Optionally, pressure transducer 23 may contain an internal amplifier positioned inside pressure transducer 23 and in the chamber between fixed plate 26 and non-sensing end 32. The internal amplifier would be connected electrically to wire 29 and fixed plate 26. The internal amplifier would amplify electrical signals generated by the movements or flexing of diaphragm 25 in relationship to fixed plate 26 which is in response to arterially-induced pressure pulsations generated in the bladders.

Referring now to FIG. 6, outer rigid cylindrical shell 170 is illustrated containing cuff 71 which includes a substantially flat, flexible, inflatable, first bladder 1 and a substantially flat, flexible, inflatable, second bladder 2 both illustrated in FIG. 7. Sensor 3 as illustrated in FIG. 6 and FIG. 7 is in fluid communication with first bladder 1 and sensor 5 as illustrated in FIG. 6 and FIG. 7 is in fluid communication with second bladder 2. As illustrated in FIG. 6 fluid passageway 6 passes through outer shall 170 and is in fluid communication with second bladder 2 as illustrated in FIG. 1 and fluid passageway 4 passes through outer shell 170 and is in fluid communication with first bladder 1 as illustrated in FIG. 1 and FIG. 7.

DETAILED DESCRIPTION OF THE MORE PREFERRED EMBODIMENT

The preferred embodiment comprises a device for detecting arterial pulsations in a subject's body comprising an outer rigid cylindrical shell to encircle a portion of a subject's body, a cuff including at least one substantially flat, flexible, inflatable, bladder, encircled and secured to the inside circumference of said shell to engage said body portion, a first tubular member having a first and second end, said first end of said tubular member engaging the interior of said bladder in a fluid-tight manner, said second end of said tubular member in fluid communication with a means for decreasing and increasing pressure in said bladder, a pressure control means cooperable with said means for decreasing and increasing pressure in said bladder and said interior of said bladder to control the pressure in said bladder, the improvement comprising a sensor in fluid communication with said interior of said bladder and responsive to arterially-induced pressure pulsations in said bladder for generating an electrical signal having an amplitude corresponsing to said pulsations in said bladder, said sensor comprising a pressure transducer chamber and a pressure transducer, said pressure transducer having an arterial pulsation sensing end in fluid communication with the interior of the bladder in a fluid-tight manner to detect arterially-induced pressure pulsations in said bladder and to generate electrical signals having an amplitude corresponding to said pulsations in said bladder and a non-sensing end in fluid communication with the interior of the said pressure transducer chamber, a pressure equalization passageway in fluid communication with the interior of said bladder and the interior of said pressure transducer chamber, said pressure equalization passageway of sufficient size to allow equalization of pressure between said bladder and said chamber sufficiently to substantially reduce inflation pressure from impending upon said pressure transducer without interferring with detection of said arterially-induced pressure pulsations by said pressure transducer thereby eliminating any interference of inflation pressure with detecting of arterially-induced pressure pulsations in said bladder by said pressure transducer.

The preferred pressure transducer is a condensed microphone. The most preferred pressure condenser is an electret condenser microphone.

The pressure equalization passageway is preferably of a sufficient size to allow from about 50.0 to about 70.0 percent pressure change between the interior of said bladder and the interior of the pressure transducer chamber to occur within about 150 to about 250 milliseconds. The more preferred size is when the pressure change is from about 60 to about 65 percent and from about 190 to about 210 milliseconds. The most preferred size is when the pressure change is 63 percent in 200 milliseconds when bladder inflation pressure in said bladder is at least about 50 mm Hg. The device may additionally contain an attenuator, said attenuator containing interior sides which coincides with exterior sides of said sensor, said attenuator containing one closed end, said closed end of said attenuator containing an attenuator passageway through said closed end of said attenuator in fluid communication with the inside of said bladder and said inside of said attenuator, said sensor in slideable contact with the interior sides of said attenuator, with the pressure transducer of said sensor in fluid communication with said attenuator passageway said attenuator passageway being of sufficient size to allow arterially-induced pressure pulsations to pass from said bladder to said sensor while allowing said amplitude of said arterially-induced pressure pulsations to be reduced when said sensor slideably moves inside said attenuator away from said bladder thereby reducing said arterially-induced pressure pulsation amplitudes allowing the use of pressure transducers with different detecting sensitivities to said amplitudes.

The more preferred embodiment comprises a device for detecting arterial pulsations for utilization in a system for determining pulse rate and systolic and diastolic blood pressure including an outer, rigid, cylindrical shell to encircle a portion of a subject's body, a first cuff including a substantially flat, flexible, inflatable, first bladder, encircled and secured to a first portion of the inside circumference of said shell to engage said body portion and a second cuff including a substantially flat, flexible, inflatable, second bladder, encircled and secured to a second portion of the inside circumference of said shell to engage said body portion, a first tubular member having a first and second end, said first end of said first tubular member engaging the interior of said first bladder in a fluid-tight manner, said second end of said first tubular member in fluid communication with a means for increasing and decreasing pressure in said first and second bladder, a second tubular member having a first and second end, said first end of said second tubular member engaging the interior of said second bladder in a fluid-tight manner, said second end of said second tubular member in fluid communication with said means for increasing and decreasing pressure in said first and second bladders, a pressure control means cooperable with said means for increasing and decreasing pressure in said first and second bladders and said interior of said second bladder to control pressure in said second and first bladders, the improvement comprising a first sensor in fluid communication with said first bladder and responsive to arterially-induced pressure pulsations in said first bladder for generating a first electrical signal having an amplitude corresponding to said first bladder pulsations, said first sensor comprising a first pressure transducer chamber and a first pressure transducer, said first pressure transducer having an arterial pulsation sensing end in fluid communication with the interior of said first bladder to detect arterially-induced pressure pulsations in said first bladder and to generate a first electrical signal having an amplitude corresponding to said first bladder pulsations and a non-sensing end of said first pressure transducer in fluid communication with the interior of said first chamber in a fluid-tight manner, a first pressure equalization passageway in said first chamber in fluid communication with the interior of said first bladder and the interior of said first pressure transducer chamber, said first pressure equalization passageway of a sufficient size to allow equalization of pressure between said first bladder and said first chamber sufficiently to substantially reduce inflation pressure from impending upon said first pressure transducer without interferring with detection of said arterially-induced pressure pulsations by said first pressure transducer thereby eliminating any interference of inflation pressure with detection of arterially-induced pressure pulsations in said first bladder by said first pressure transducer, a second sensor in fluid communication with said second bladder and responsive to arterially-induced pressure pulsations in said second bladder for generating a second electrical signal having an amplitude corresponding to said second bladder pulsations, said second sensor comprising a second pressure transducer chamber and a second pressure transducer, said second pressure transducer having an arterial pulsation sensing end in fluid communication with the interior of the second bladder to detect arterially-induced pressure pulsations in said second bladder and generate a second electrical signal having an amplitude corresponding to said second bladder pulsations and a non-sensing end of said second pressure transducer in fluid communication with the interior of said second chamber in a fluid-tight manner, a second pressure equalization passageway through a wall in said second chamber in fluid communication with the interior of said second bladder and the interior of said second pressure transducer chamber, said second pressure equalization passageway of a sufficient size to allow equalization of pressure between said second bladder and said second chamber sufficiently to substantially reduce inflation pressure from impending upon said second pressure transducer without interferring with detection of said arterially-induced pressure pulsations by said second pressure transducer thereby eliminating any interference of inflation pressure with detection of arterially-induced pressure pulsations in said second bladder by said second pressure transducer.

The first pressure transducer is preferably a condenser microphone. More preferable the first pressure transducer is an electret condenser microphone.

A most preferred pressure transducer is available as Panasonic Omnidirectional Elected Condenser Microphone Cartridge as part No. WM-063T. The most preferred pressure transducer has a sensitivity of $-64\pm3$ dB (OdB—IV/ubar, 1 KHz), low impedance, Omnidirectional, frequency range 20-20,000 Hz.

The first pressure equalization passageway is preferable of a sufficient size to allow from about 50.0 to about 70.0 percent pressure change between the interior of said first bladder and the interior of said first pressure transducer chamber to occur within from about 150 to about 250 milliseconds. The more preferred size is where the pressure change is 63.0 percent in 200 milliseconds when bladder inflation pressure in said bladder is at least 50 mm Hg.

The device additionally contains a first attenuator, said first attenuator containing interior sides which coincide with the exterior sides of said first sensor, said first attenuator containing one closed end, said closed end of said first attenuator containing a first attenuator passageway through said closed end of said attenuator in fluid communication with the inside of said first bladder and said inside of said first attenuator, said first sensor in slideable contact with the interior sides of said first attenuator with the pressure transducer of said first sensor in fluid communication with said first attenuator passageway, said first attenuator passageway being of a sufficient size to allow arterially-induced pressure pulsations to pass from said first bladder to said first sensor while allowing said amplitude of said arterially-induced pressure pulsations to be reduced when said first sensor slideable moves inside said first attenuator away from said first bladder thereby reducing said arterially-induced pressure pulsation amplitudes allowing the use of pressure transducers in said first sensor with different detecting sensitivities to said amplitudes.

Preferably the first sensor generated first electrical signals are processed to calculate the systolic blood pressure. Preferably the second sensor generated second electrical signals are processed to calculate the diastolic blood pressure. Preferably the first and second sensor generated first and second electrical signals are processed to calculate pulse rate.

The second pressure transducer is preferably a condenser microphone. More preferably the second pressure transducer is an electret condenser microphone.

The second pressure equalization passageway is preferably of a sufficient size to allow from about 50.0 to about 70.0 percent pressure change between the interior of said second bladder and the interior of said second pressure transducer chamber to occur within from about 150 to about 250 milliseconds. More preferably the pressure change is 63.0 percent and in 200 milliseconds when bladder inflation pressure in said bladder is at least about 50 mm Hg.

The device additionally contains a second attenuator, said second attenuator containing interior sides which coincide with the exterior sides of said second sensor, said second attenuator containing one closed end, said closed end of said second attenuator containing a second attenuator passageway through said closed end of said second attenuator in fluid communication with the inside of said second bladder and said inside of said second attenuator, said second sensor in slideable contact with the interior sides of said second attenuator with the pressure transducer of said second sensor in fluid communication with said second attenuator passageway, said second attenuator passageway being of a sufficient size to allow arterially-induced pressure pulsations to pass from said second bladder to said second sensor while allowing said amplitude of said arterially-induced pressure pulsations to be reduced when said first sensor slideably moves inside said second attenuator away from said second bladder thereby reducing said arterially-induced pressure pulsation amplitudes allowing the use of pressure transducers in said first sensor with different detecting sensitivities to said amplitudes.

A preferred embodiment comprises a method for automatically determining pulse rate and systolic and diastolic blood pressure of a subject including a device employing an automatic arterial pulsation monitoring cuff to encircle a portion of a subject's body containing at least a first and second selectively inflatable bladders each containing a sensor responsive to arterially-induced pressure pulsations in said cuff for generating electrical signals having amplitudes corresponding to the pulsations in said bladders, said second bladder in fluid communication with a sensor responsive to pressure in said second bladder for generating electrical signals corresponding to the pressure in said second bladder, said bladders interconnected with a pressurizing system, all of said sensors connected electrically to a system for automatically processing the electrical signals from said sensors and automatically inflating and deflating the bladders and a means for calculating the pulse rate and the systolic and diastolic pressure of the subject comprising the steps of:
  (a) positioning said first and second bladders in said cuff in relationship to each other such that said second bladder is an occluding bladder;
  (b) secondly simultaneously inflating at least said first and second bladders to a determined pressure at which inflation ceases and at which said second occluding bladder occludes blood flow resulting in said sensor in said first bladder sensing no arterially induced pressure pulsation amplitudes;
  (c) thirdly deflating said first and second bladders at a predetermined rate;
  (d) during steps (b) and (c) continuously generating electrical signals having an amplitude corresponding to the pulsations in the bladders and the pressure in said second bladder, and measuring the time duration between each pulsation;
  (e) during steps (b) through (c) monitoring continuously and signals and said time durations;
  (f) during steps (b) through (c) storing said signals and said time durations;
  (g) fourthly terminating the deflating step (c) at a predetermined pressure and then releasing the pressure from said first and second bladders;
  (h) then processing said stored signals and said time durations to determine the subject's pulse rate, systolic blood pressure and diastolic blood pressure comprising the steps of:
    (1) first determining the systolic pressure of the subject by determining inflation pressure in the second bladder when a first pulsation is detected in said first bladder after deflation begins in step (c);

(2) secondly, examining amplitudes of all pulsations detected in said second bladder during step (c) and first determining an increase in amplitudes and then a decrease in amplitudes and then constant amplitudes, and then determining the diastolic pressure of the subject by determining the inflation pressure in said second bladder when a first pulsation at the beginning of the constant amplitudes is detected in said second bladder and (3) examining the time duration between all pulsations during step (c) and then calculating the pulse rate of the subject.

More preferably the time duration between the maximum amplitudes of the last eight arterially-induced pressure pulsations in the second bladder before the termination of the deflation step are measured and then used to determine the average time duration between pulsations. The average time duration is then divided into 60 to calculate the number of pulses per minute i.e., pulse rate.

The pressure in step (b) preferably increases to about 50 mm Hg before steps (d), (e) and (f) begin.

In addition to the above method to additionally determine the occluding pressure of the subject by examining amplitudes of all pulsations detected in said second bladder in step (b) and first determining increase in amplitudes of said pulsations and then a decrease in amplitudes, and then determining the occluding pressure of the subject by determining the inflation pressure in said second bladder when the amplitude in the second bladder drops below a predetermined level and pulsations cease in said first bladder. Said occluding pressure is the predetermined pressure at which inflation ceases in step (b).

The predetermined rate of deflating in step (c) is preferably from about 2 to about 4 mm Hg per second.

The preferred predetermined pressure for terminating the deflation step (g) is preferably 50 mm Hg.

The predetermined pressure for terminating the deflation step (g) is preferably 50 mm Hg.

When the words "impending upon said pressure transducer" is used herein, it is meant that the inflation pressure in the bladder is sufficient to force the pressure transducer diaphragm located in the pressure transducer into a fixed shape or position such that the diaphragm is unable to respond, i.e., move or flex, in response to arterially-induced pressure pulsations generated in the bladder.

When the words "pressure equalization" is used herein it is meant to describe the pressure equalization passageway. Pressure equalization means that this passageway equalizes the pressure on both sides of the wall through which the passageway is placed. When the terms "interference of inflation pressure with detecting of arterially-induced pressure pulsations" is used herein, it is meant to mean that the pressure in the bladder impends upon the pressure transducer diaphragm located in the pressure transducer and prevents the diaphragm from responding or detecting arterially-induced pressure pulsations. As to determining the size or diameter of the pressure equalization passageway, its size or the diameter depends upon the volume of the pressure transducer chamber. The size or diameter of the passageway is in direct proportion to the volume of the pressure transducer chamber. The passageway size or diameter is calculated by obtaining a time constant. This time constant is obtained by first creating a pressure change at one end of the passageway. This pressure change is measured at the other end of the passageway. The passageway size or diameter is such that the most preferred pressure change should equal 63% of the created pressure change in most preferably 200 milliseconds. This is the time constant of the pressure change.

For example, a pressure changing measuring device is placed at one end of a passageway and that end is labeled (A). This measuring device may be one made by I.C. Sensors, Inc. At the other end labeled (B) of the passageway the pressure change is also measured along with the time required to make that change. A sudden increase in pressure is created at end (A) of the passageway. This increase in pressure is measured. At the other end (B) of the passageway, the change in pressure is also measured along with determining the number of milliseconds it takes for the pressure at end (B) to reach (the most preferred change) 63% of the change in the pressure which occurred at end (A). The most preferred time is 200 milliseconds. As discussed, without this pressure equalization passageway. as the inflation pressure increases in the bladder, that pressure presses against the pressure transducer diaphragm within the pressure transducer. The diaphragm cannot respond readily if large pressures are pushing or holding the diaphragm in a fixed position. The pressure equalization passageway by equalizing pressure on both sides of the pressure transducers diaphragm allows the pressure transducer to respond to small pressure changes while adjusting to large pressure changes across the pressure transducer. The larger the size or diameter of the pressure equalization passageway in relationship to the pressure transducer chamber, the faster the system will adjust to larger pressure increases and the less sensitive the system will become to small pressure changes due to the arterially-induced pressure pulsations. Consequently the size or diameter of the pressure equalization passageway is critical.

It will be appreciated that the foregoing sets forth preferred and illustrative embodiments of the principles of the present invention, but that numerous alternative embodiments will occur to those of ordinary skill in the art without departure from the spirit or the scope of the principles of the present invention. Likewise, variation of sizes of tubes, interconnecting the fluid volume chamber with the cuffs or bladders, can be utilized to accentuate the differentials which would otherwise exist. Further, variations of locations of sensors within the cuffs or bladders may vary.

We claim:

1. a device for detecting arterial pulsations in a subject's body comprising an outer rigid cylindrical shell to encircle a portion of a subject's body, a cuff including at least one substantially flat, flexible, inflatable, bladder, encircled and secured to the inside circumference of said shell to engage said body portion, a first tubular member having a first and second end, said first end of said tubular member engaging the interior of said bladder in a fluid-tight manner, said second end of said tubular member in fluid communication with a means for decreasing and increasing pressure in said bladder, a pressure control means cooperable with said means for decreasing and increasing pressure in said bladder and said interior of said bladder to control the pressure in said bladder, the improvement comprising a sensor in fluid communication with said interior of said bladder and responsive to arterially-induced pressure pulsations in said bladder for generating an electrical signal having an amplitude corresponding to said pulsations in said bladder, said sensor comprising a pressure transducer chamber and a pressure transducer, said pressure transducer having an arterial pulsation sensing end in fluid communication with the interior of said bladder in a fluid-tight manner to detect arterially-induced pressure pulsations in said bladder and to generate electrical signals having an amplitude corresponding to said pulsations, said bladder and a non-sensing end in fluid communication with the interior of the said pressure transducer chamber, a pressure equalization passageway in fluid communication with the interior of said bladder and the interior of said pressure transducer chamber, said pressure equalization passageway of sufficient size to allow equalization of pressure between said bladder and said chamber sufficiently to substantially reduce inflation pressure from impending upon said pressure transducer without interfering with detection of said arterially-induced pressure pulsations by said pressure transducer thereby eliminating any interference of inflation pressure with detecting of arterially-induced pressure pulsations in said bladder by said pressure transducer.

2. The device according to claim 1 wherein said pressure transducer is a condenser microphone.

3. The device according to claim 2 wherein said condenser microphone is an electret condenser microphone.

4. The device according to claim 1 wherein said pressure equalization passageway is of a sufficient size to allow from about 50.0 to about 70.0 percent pressure change between the interior of said bladder and the interior of the pressure transducer chamber to occur within about 150 to about 250 milliseconds.

5. The device according to claim 4 wherein said pressure change is from about 60 to about 65 percent and from about 190 to about 210 milliseconds.

6. The device according to claim 5 wherein the pressure change is 63 percent in 200 milliseconds when bladder inflation pressure in said bladder is at least about 50 mm Hg.

7. The device according to claim 1 wherein said device additionally contains an attenuator, said attenuator containing interior sides which coincides with exterior sides of said sensor, said attenuator containing one closed end, said closed end of said attenuator containing an attenuator passageway through said closed end of said attenuator in fluid communication with the interior of said bladder and said interior sides of said attenuator, said sensor in slideable contact with the interior sides of said attenuator, with the pressure transducer of said sensor in fluid communication with said attenuator passageway, said attenuator passageway being of sufficient size to allow arterially-induced pressure pulsations to pass from said bladder to said sensor while allowing said amplitude of said arterially-induced pressure pulsations to be reduced when said sensor slideably moves inside said attenuator away from said bladder thereby reducing said arterially-induced pressure pulsation amplitudes allowing the use of pressure transducers with different detecting sensitivities to said amplitudes.

8. A device for detecting arterial pulsations for utilization in a system for determining pulse rate and systolic and diastolic blood pressure including an outer, rigid, cylindrical shell to encircle a portion of a subject's body, a first cuff including a substantially flat, flexible, inflatable, bladder, encircled and secured to a first portion of the inside circumference of said shell to engage said body portion and a second cuff including a substantially flat, flexible, inflatable, bladder, encircled and secured to a second portion of the inside circumference of said shell to engage said body portion, a first tubular member having a first and second end, said first end of said first tubular member engaging the interior of said first bladder in a fluid-tight manner, said second end of said first tubular member in fluid communication with a means for increasing and decreasing pressure in said first and second bladders, a second tubular member having a first and second end, said first end of said second tubular member engaging the interior of said second bladder in a fluid-tight manner, said second end of said second tubular member in fluid communication with said means for increasing and decreasing pressure in said first and second bladders, a pressure control means cooperable with said means for increasing and decreasing pressure in said first and second bladders and said interior of said second bladder to control pressure in said second and first bladders, the improvement comprising a first sensor in fluid communication with said first bladder and responsive to arterially-induced pressure pulsations in said first bladder for generating a first electrical signal having an amplitude corresponding to said pulsations in first said bladder, said first sensor comprising a first pressure transducer chamber and a first pressure transducer, said first pressure transducer having an arterial pulsation sensing end in fluid communication with the interior of said first bladder to detect arterially-induced pressure pulsations in said first bladder and to generate a first electrical signal having an amplitude corresponding to said pulsations in first bladder and a non-sensing end of said first pressure transducer in fluid communication with the interior of said first chamber in a fluid-tight manner, a first pressure equalization passageway in said first chamber in fluid communication with the interior of said first bladder and the interior of said first pressure transducer chamber, said first pressure equalization passageway of a sufficient size to allow equalization of pressure between said first bladder and said first chamber sufficiently to substantially reduce inflation pressure from impending upon said first pressure transducer without interfering with detection of said arterially-induced pressure pulsations by said first pressure transducer thereby eliminating any interference of inflation pressure with detection of arterially-induced pressure pulsations in said first bladder by said first pressure transducer, a second sensor in fluid communication with said second bladder and responsive to arterially-induced pressure pulsations in said second bladder for generating a second electrical signal having an amplitude corresponding to said second bladder pulsations, said second sensor comprising a second pressure transducer chamber and a second pressure transducer, said second pressure transducer having an arterial pulsation sensing end in fluid communication with the interior of the second bladder to detect arterially-induced pressure pulsations in said second bladder and generate a second electrical signal having an amplitude corresponding to said second bladder pulsations and a non-sensing end of said second pressure transducer in fluid communication with the interior of said second chamber in a fluid-tight manner, a second pressure equalization passageway through a wall in said second chamber in fluid communication with the interior of said second bladder and the interior of said second pressure transducer chamber, said second pressure equalization passageway of a sufficient size to allow equalization of pressure between said second bladder and said second chamber sufficiently to substantially reduce inflation pressure from impending upon said second pressure transducer without interfering with detection of said arterially-induced pressure pulsations by said second pressure transducer thereby eliminating any interference of inflation pressure with detection of arterially-induced pressure pulsations in said second bladder by said second pressure transducer.

9. The device according to claim 8 wherein said first pressure transducer is a condenser microphone.

10. The device according to claim 9 wherein said condenser microphone is an electret condenser microphone.

11. The device according to claim 8 wherein said first pressure equalization passageway is of a sufficient size to allow from about 50.0 to about 70.0 percent pressure change between the interior of said first bladder and the interior of said first pressure transducer chamber to occur within from about 150 to about 250 milliseconds.

12. The device according to claim 11 wherein the pressure change is 63.0 percent in 200 milliseconds when bladder inflation pressure in said bladder is at least 50 mm Hg.

13. The device according to claim 8 wherein said device additionally contains a first attenuator, said first attenuator containing interior sides which coincide with the exterior sides of said first sensor, said first attenuator containing one closed end, said closed end of said first attenuator containing a first attenuator passageway through said closed end of said attenuator in fluid communication with the interior of said first bladder and said interior sides of said first attenuator, said first sensor in slideable contact with the interior sides of said first attenuator with the pressure transducer of said first sensor in fluid communication with said first attenuator passageway, said first attenuator passageway being of a sufficient size to allow arterially-induced pressure pulsations to pass from said first bladder to said first sensor while allowing said amplitude of said arterially-induced pressure pulsations to be reduced when said first sensor slideably moves inside said first attenuator away from said first bladder thereby reducing said arterially-induced pressure pulsation amplitudes allowing the use of pressure transducers in said first sensor with different detecting sensitivities to said amplitudes.

14. The device according to claim 8 wherein said second pressure transucer is a condenser microphone.

15. The device according to claim 14 wherein said condenser microphone is an electret condenser microphone.

16. The device according to claim 8 wherein said second pressure equalization passageway is of a sufficient size to allow from about 50.0 to about 70.0 percent pressure change between the interior of said second bladder and the interior of said second pressure transducer chamber to occur within from about 150 to about 250 milliseconds.

17. The device according to claim 16 wherein the pressure change is 63.0 percent and in 200 milliseconds when bladder inflation pressure in said bladder is at least about 50 mm Hg.

18. The device according to claim 8 wherein said device additionally contains a second attenuator, said second attenuator containing interior sides which coincide with the exterior sides of said second sensor, said second attenuator containing one closed end, said closed end of said second attenuator containing a second attenuator passageway through said closed end of said second attenuator in fluid communication with the interior of said second bladder and said interior sides of said second attenuator, said second sensor in slideable contact with the interior sides of said second attenuator with the pressure transducer of said second sensor in fluid communication with said second attenuator passageway, said second attenuator passageway being of a sufficient size to allow arterially-induced pressure pulsations to pass from said second bladder to said second sensor while allowing said amplitude of said arterially-induced pressure pulsations to be reduced when said first sensor slideably moves inside said second attenuator away from said second bladder thereby reducing said arterially-induced pressure pulsation amplitutes allowing the use of pressure transducers in said first sensor with different detecting sensitivities to said amplitudes.

19. A method for automatically determining pulse rate and systolic and diastolic blood pressure of a subject including a device employing an automatic arterial pulsation monitoring cuff to encircle a portion of said subject's body containing at least a first and second selectively inflatable bladders each containing a sensor reponsive to arterially-induced pressure pulsations in said cuff for generating electrical signals having amplitudes corresponding to the pulsations in said bladders, said second bladder in fluid communication with a sensor responsive to pressure in said second bladder for generating electrical signals corresponding to the pressure in said second bladder, said bladders interconnected with a pressurizing system, all of said sensors connected electrically to a system for automatically processing the electrical signals from said sensors and automatically inflating and deflating the bladders and a means for calculating the pulse rate and the systolic and diastolic pressure of the human subject comprising the steps of:

(a) positioning said first and second bladders in said cuff in relationship to each other such that said second bladder is an occluding bladder;

(b) secondly simultaneously inflating at least said first and second bladders to a determined pressure at which inflation ceases and at which said second occluding bladder occludes blood flow resulting in said sensor in said first bladder sensing no arterially induced pressure pulsation amplitudes;

(c) thirdly deflating said first and second bladders at a predetermined rate;

(d) during steps (b) and (c) continuously generating electrical signals having an amplitude corresponding to the pulsations in the bladders and the pressure in said second bladder and measuring the time duration between each pulsation;

(e) during steps (b) through (c) monitoring continuously said signals and said time durations;

(f) during steps (b) through (c) storing said signals and said time durations;

(g) fourthly terminating the deflating step (c) at a predetermined pressure and then releasing the pressure from said first and second bladders;

(h) then processing said stored signals and said time durations to determine the subject's pulse rate, systolic blood pressure and diastolic blood pressure comprising the steps of:

(1) first determining the systolic pressure of the subject by determining inflation pressure in the second bladder when a first pulsation is detected in said first bladder after deflation begins in step (c);

(2) secondly, examininig amplitudes of all pulsations detected in said second bladder during step (c) and first determining an increase in amplitudes and then a decrease in amplitudes and then constant amplitudes, and then determining the diastolic pressure of the subject by determining the inflation pressure in said second bladder when a first pulsation at the beginning of the constant amplitudes is detected in said second bladder; and (3) examining the time duration between all pulsations during step (c) and then caculating the pulse rate of the subject.

20. The method according to claim 19 wherein the pressure in step (b) increases to about 50 mm Hg before steps (d), (e) and (f) begin.

21. The method according to claim 20 comprising the additional step of determining the occluding pressure of the subject by examining amplitudes of all pulsations detected in said second bladder in step (b) and first determining an increase in amplitudes of said pulsations and then a maximum amplitude and then a decrease in amplitudes, and then determining the occluding pressure of the subject by determining the inflation pressure in said second bladder when these amplitudes drop below a predetermined level and pulsations cease in said first bladder, said predetermined level comprises one-half of said maximum amplitude and said occluding pressure is the predetermined pressure at which inflation ceases in step (b).

22. The method according to claim 21 wherein in step (c) the predetermined rate of deflating is from about 2 to about 4 mm Hg per second.

23. The method according to claim 22 wherein the predetermined pressure for terminating the deflation step (g) is 50 mm Hg.

* * * * *